United States Patent [19]

Verlaan et al.

[11] Patent Number: 4,855,428
[45] Date of Patent: Aug. 8, 1989

[54] TRIAZINE PEROXIDES

[75] Inventors: Johannes P. J. Verlaan, Deventer; Wilhelmus M. Beijleveld, Olst, both of Netherlands

[73] Assignee: Akzo N.V., Arnhem, Netherlands

[21] Appl. No.: 51,753

[22] Filed: May 20, 1987

[30] Foreign Application Priority Data

Jun. 11, 1986 [NL] Netherlands ............... 8601509

[51] Int. Cl.$^4$ .................. C07D 251/30; C07D 251/34
[52] U.S. Cl. .................................... 544/219; 525/281
[58] Field of Search ............................ 544/219

[56] References Cited

U.S. PATENT DOCUMENTS 3,980,629 9/1976 Sacrini et al. ................ 544/219

FOREIGN PATENT DOCUMENTS

| | | | |
|---|---|---|---|
| 58-83008 | 5/1983 | Japan | 544/219 |
| 58-76405 | 9/1983 | Japan | 544/219 |
| 60-206849 | 10/1985 | Japan | 544/219 |
| 60-208309 | 10/1985 | Japan . | |
| 60-208316 | 10/1985 | Japan . | |
| 1456341 | 11/1976 | United Kingdom | 544/219 |
| 2081282 | 2/1982 | United Kingdom | 544/219 |
| 8002285 | 10/1980 | World Int. Prop. O. | 544/219 |

OTHER PUBLICATIONS

Safford et al., CA, vol. 68, 1968, 68:22554.
Sorokin et al., CA, vol. 92, 1980, 92:43353j.
"Organic Peroxides-XIX", Tetrahdron, vol. 34, pp. 1231-1233.

Primary Examiner—John M. Ford
Attorney, Agent, or Firm—Oliff & Berridge

[57] ABSTRACT

Organic peroxides having at least one carbon-carbon double bond, e.g. 2-t-amylperoxy-4,6-diallyloxy-1,3,5-triazine, and the use of such organic peroxides as crosslinking agents for polymers are disclosed. The organic peroxides of the current invention allow polymer crosslinking at elevated temperatures. The disclosed organic peroxides are especially useful in processes for crosslinking polymers and co-polymers of ethylene.

3 Claims, No Drawings

TRIAZINE PEROXIDES

The invention relates to organic peroxides which have at least one carbon-carbon double bond in the molecule and to a process for cross-linking polymers with these peroxides. Such peroxides and a process of the type indicated above are disclosed in U.S. Pat. No. 3,980,629. According ot it, the use of unsaturated peroxyketals as crosslinking agents leads to cross-linked polymers that are practically odourless and do no exhibit blooming.

Polymers having those properties are desirable in that, as is generally known, the more or less volatile decomposition products formed from dicumyl peroxide, which is often used in practice for cross-linking and degradation purposes, will lead to polymers which have an unpleasant smell and display blooming, which is objectionable to their applicability, for instance as packaging material for foodstuffs.

To the peroxyketals described in said U.S. Patent, however, there is the disadvantage that the temperature at which they are incorporated into a polymer is subject to restrictions in view of the rick of premature decomposition. This drawback manifests itself particularly in the cross-linking of those polymers, such as elastomers, into which the peroxide, and other additives, if desired, are to be mixed in at elevated temperature prior to the polymer mass being shaped. To prevent premature cross-linking (scorching), the temperature at which these well-known peroxides are allowed to be processed is relatively low. This low temperature processing is detrimental to the viscosity and, hence, the processability of the polymer mass cross-linked. As cross-linking agents, these peroxyketals are therfore not satisfactory alternatives to dicumyl peroxide. The invention envisages the elimination of these drawbacks. It provides peroxides that are not subject to the temperature limitations of said peroxyketals, but do retain the favourable properties of these peroxyketals with respect to smell and blooming of the polymeric end products (see above) and as crosslinking and degrading agents form a good alternative to dicumyl peroxide.

It should be noted that for use as a cross-linking agent for rubber an unsaturated peroxide is known from Wp 8,002,285, viz. 1-methacrylate-1-t-butyl peroxyethane. It has been found, however, that the data provided in said publication do not make it possible for this peroxide to be reproduced.

It should also be noted that peroxides having a triazine nucleus in the molecule are disclosed, among other places, in Japanese Patent Application Nos. 58076405, 58083008, 60206849, 60208309 and 60208316, British Patent Specification No. 1456341 and Tetrahedron, Vol. 34 pp. 1231–1233 (1978). These publications, however, do not describe peroxides which have one or more carbon-carbon double bonds in the molecule. Unlike the unsaturated peroxides of the current invention, use of such saturated peroxides as crosslinking agents will produce polymers which display blooming and have unpleasant odours.

The peroxides according to the invention correspond to the general formula:

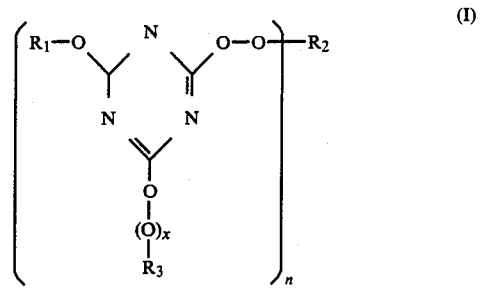
(I)

wherein
when $n=1$,
$R_1$ is selected from the group consisting of an allyl group, a methallyl group and a crotyl group,
$R_2$ is selected from the group consisting of an unsubstituted alkyl group, an alkyl group substituted with at least one hydroxyl group, an unsubstituted alkenyl group, an alkenyl group substituted with at least one hydroxyl group, an unsubstituted aralkyl group, and an aralkyl group substituted on the aromatic ring with at least one substituent selected from the group consisting of alkyl groups, aleknyl groups and mixtures thereof, $R_2$ having 4–20 carbon atoms when $R_2$ is non-aromatic and 7–20 carbon atoms when $R_2$ is aromatic,
x is selected from the group consisting of 0 and 1,
when $x=0$, $R_3=R_1$,
when $x=1$, $R_3=R_2$; and
when $n=2$,
$R_1$ is selected from the group consisting of an allyl group, a methallyl group and a crotyl group,
$R_2$ is selected from the group consisting of an unsubstituted alkylene; an unsubstituted alkynylene; and alkylene substituted with one or more substituents selected from the grup consisting of alkyl groups, alkenyl groups and mixtures thereof; and an alkynylene substituted with one or more substituents selected from the group consisting of alkyl groups, alkenyl groups and mixtures thereof, $R_2$ having 4–20 carbon atoms;
$x=0$ and $R_3=R_1$.

The alkyl groups and alkenyl groups in $R_2$ and the alkyl part of the aralkyl group may be branched or unbranched.

THE PRESENT PEROXIDES

The peroxides according to the invention may be prepared in a simple manner by reacting 2,4,6-trichloro-1,3,5-triazine (cyanuric chloride) with 1 or 2 equivalents of allyl alchol, methallyl alcohol or crotyl alcohol under alkaline conditions in an aqueous medium and by reacting the resulting product, preferably after purification and also under aqueous, alkaline conditions and preferably in the presence of an inert, organic solvent, with an organic hydroperoxide ROOH, wherein R has the meansing indicated above for $R_2$. The temperature at which these reactions are carried out is generally in the range of 25° to 40° C.

Non-exclusive examples of suitable bases which may be used in the current invention include sodium hydroxide and potassium hydroxide.

Non-exclusive examples of suitable organic solvents which may be used in the current invention include dichloromethane, n-heptane, toluene, cyclohexane and diethyl ether.

Non-exclusive examples of the hydroperoixdes which may be used in the current invention include:
t-butyl hydroperoxide,
t-amyl hydroperoxide,
2,4,4-trimethylpentyl-2-hydroperoxide,
4-hydroxy-2-methylpentyl-2-hydroperoxide,
2-methyl-3-buten-2-yl hydroperoxide,
2-phenylpropyl-2-hydroperoxide (=cumyl hydroperoxide),
2-(p-methylphenyl)propyl-2-hydroperoxide,
2-(p-isopropylphenyl)propyl-2-hydroperoxide,
2-(m-isopropylphenyl)propyl-2-hydroperoxide,
2-(p-isopropenylphenyl)propyl-2-hydroperoxide,
2-(m-isopropenylphenyl)propyl-2-hydroperoxide,
2,5-dimethyl-2,5-dihydroperoxy hexane, and
2,5-dimethyl-2,5-dihydroperoxy hexyne.

In view of the active oxygen content of the peroxide and synthetic accessibility, preference is given to those peroxides of the general formula I wherein:
$n=1$,
$R_1$ is an allyl group and
$R_2$ is selected from the group consisting of an unsubstituted alkyl group, an alkyl group substituted with at least one hydroxyl group, an unsubstituted alkenyl group, an alkenyl group substituted with at least one hydroxyl group, an unsubstituted aralkyl group, and an aralkyl group substituted on the aromatic ring with at least one substituent selected from the group consisting of alkyl groups, alkenyl groups and mixtures thereof, $R_2$ having 4–8 carbon atoms when $R_2$ is non-aromatic and 9–12 carbon atoms when $R_2$ is aromatic.

Non-exclusive examples of particularly suitable peroxides according to to the invention are:
2-t-butylperoxy-4,6-diallyloxy-1,3,5-triazine
2,4-di-t-butylperoxy-6-allyloxy-1,3,5-triazine,
2-(2-methyl-3-buten-2-ylperoxy)-4,6-diallyloxy-1,3,5-triazine,
2,4-di(e-methyl-3-buten-2-ylperoxy)-6-allyloxy-1,3,5-triazine and
2-[2-(m-isopropenylphenyl)propyl-2-peroxy]-4,6-diallyloxy-1,3,5-triazine.

CROSS-LINKING OF POLYMERS

As mentioned above, the present peroxides may with advantage be used in high-melting polymers, such as elastomers, without the risk of premature cross-linking during the processing phase, i.e. the phase of mixing in the peroxide and moulding the polymer mass immediately preceding the cross-linking phas. A non-exclusive examples of these polymers may be mentioned polymers and copolymers of ethylene, such as polyethylene, ethylene vinyl acetate copolymers, copolymers of ethylene and propylene (EPM) and copolymers of ethylene, propylene and diene monomer (EPDM). But the advantages to the present peroxides are not limited to use in high-melting polymers. The prsent peroxides also may with advantage be used in low-melting polymers. As a result, the polymer mass obtained may advantageously be exposed to relatively high temperatures, so that low viscosity and, hence, satisfactory processability are obtained.

Non-exclusive examples of polymers which may be cross-linked in accordance with the present process, in addition to the polymers mentioned before, include chlorosulphonated polyethylene, chlorinated polyethylene, polybutene-1, polyisobutene, polybutadiene, polyisoprene, polychloroprene, butadiene styrene copolymers, natural rubber, polyacrylate rubber, butdiene acrylonitrile copolymers, acrylonitrile-butadien-styrene terpolymers, silicone rubber, polyurethanes and polysulphides.

It is preferred that the present process should be applied for cross-linking polyethylene, EPM and EPDM.

To the polymer to be cross-linked is generally added 0.1–10% by weight, and preferably 1–3% by weight of the presen peroxide; also combinations of peroxides according to the invention may be used.

Moreover, to the polymer to be cross-linked there may be added various agents commonly employed in cross-linking processes, such as aptioxidants, pigments, UV stabilizers, fillers, plasticizers, etc. in amounts commonly used for these purposes.

The temperature at which the present peroxides may be mixed into polymeric material without there occurring any premature crosslinking is generally in the range of 25° to 130° C. The temperature at which subsequent cross-linking is carried out is generally in the range of 150° C. to 220° C., preferably 160°–190° C.

For carrying out the process according to the invention use may be made of the techniques commonly applied to cross-linking reactions in appropriate equipment.

The invention will be further described in the following examples.

EXAMPLE 1

Preparation of
2-t-butylperoxy-4,6-diallyloxy-1,3,5-triazine
(Compound 1)

To a mixture of 14 g of an aqueous solution containing 70% by weight of t-butyl hydroperoxide and 40 g of an aqueous solution containing 11% by weight of sodium hydroxide was added a solution of 19 g of 2-chloro-4,6-diallyloxy-1,3,5-triazine in 30 ml of dichloromethane, after which the reaction mixture was stirred for 4 hours at 35° C. Subsequently, the organic phase was separated and successively washed with dilute, aqueous sodium hydroxide and water, after which the dichloromethane was removed by distillation under reduced pressure. Obtained wree 23 g (yield 100%) of product in the form of a colourless liquid having an active oxygen content of 5.65% (calculated: 5.69%). The structure of Compound 1 was confirmed by NMR and IR analyses.

EXAMPLE 2

Preparation of
2-t-amylperoxy-4,6-diallyloxy-1,3,5-triazine
(Compound 2)

The procedure described in Example 1 was repated, except that use was made of an equimolar amount of t-amyl hydroperoxide instead of t-butyl hydroperoxide. Obtained was a colourless liquid in a yield of 95% and having an active oxygen content of 5.31% (calculated: 5.42%). The structure of Compound 2 was confirmed by NMR and IR analyses.

EXAMPLE 3

Preparation
2-(2-4,4-trimethylpenytl-2-peroxy)4,6-diallyloxy-1,3,5-triazine (Compound 3)

The procedure described in Example 1 was repeated, except that use was made of an equimolar amount of 2,4,4-trimethylpentyl-2-hydroperoxide instead of t-butyl hydroperoxide. Obtained was a colour less liquid in a yield of 65% and having an active oxygen content of 3.96% (calculated: 4.74%). The structure of Compound 3 was confirmed by NMR and IR analyses.

EXAMPLE 4

Preparation of
2-(40-hydroxy-2mtheylpentyl-2-peroxy)-4,6-diallyloxy-1,3,5-triazine (Compound 4)

The procedure described in Example 1 was repeated, except that use was made of an equimolar amount of 4-hydroxy-2methylpentyl-2-hydroperoxide instead of t-butyl hydroperoxide. Obtained was a colourless liquid in a yield of 81% and having an active oxygen content of 4.57% (calculated: 4.92%). The structure of Compound 4 was confirmed by NMR and IR analyses.

EXAMPLE 5

Preparation of
2,4-di-t-butylperoxy-6-allyloxy-1,3,5-triazine (Compound 5)

The procedure described in Example 1 was repeated, except that use was made of a mixture of 19 g of an aqueous solution containing 70% by weight of t-butyl hydroperoxide and 24 g of an aqueous solution containing 25% by weight of sodium hydroxide, to which mixture a solution of 14 g of 2,4-dicholor-6-allyloxyl,3,5-triazine in 15 ml of dichloromethane was added. Obtained were 18 g (yield 96%) of colourless liquid having an active oxygen content of 9.68% (calculated: 10.21%). The structure of Compound 5 was confirmed by NMR and IR analyses.

EXAMPLE 6

Preparation of
2,5-dimethyl-2,5-di(4,6-diallyloxytriazinyl-2-peroxy)-benxane (Compound 6)

The procedure described in Example 1 was repeated, except that use was made of an equimolar amount of 2,5-dimethyl-2,5-dihydroperoxy hexane instead of t-butyl hydroperoxide. Obtained was a colourless liquid in a yield of 74% and having an active oxygen content of 5.34% (calculated: 5.72%). The structure of Compound 6 was confirmed by NMR and IR analyses.

EXAMPLE 7

Preparation of
2,5-dimethyl-2,5-di(4,6-diallyloxytriazinyl-2-peroxy)-hexyne (Compound 7)

The procedure described in Example 1 was repeated, except that use was made of an equivalent amount of 2,5-dimethyl-2,5-dihydroperoxy hexyne instead of t-butyl hydroperoxide. Obtained was a colourless liquid in a yield of 81% and having an active oxygen content of 5.41% (calculated:5.77%). The structure of compound 7 was confirmed by NMR and IR analyses.

EXAMPLE 8

Of the peroxides described in the preceding exmaples the permissible processing temperature was determined as follows.

Over a period of 5 minutes, 0.01 equivalent of the peroxide (-0.01 mole of the Compounds 1-4, and 0.005 moles of Compounds 5-7, respectively) was mixed with 100 g of ethylene-propylene copolymer (EPM) on a roll mill at a friction of 1:1.2 and at a temperature of 50°-70° C. Of the resulting mixture, the cross-linking behaviour was subsequently determined with the aid of a Göttfert Elastograph in the manner described in Katushcuk and Cummi 29(5/6) 341-352 (1976). In this determination, the mixture to be cross-linked is embedded in a heated chamber, the lower half of which is oscillatory. During cross-linking, the increase is registered in the torque on the lower chamber half as a result of the increase in viscosity of the cross-linking mixture as a function of time. This increase in torque is expressed in the parameters $t_{10}$ and $t_{90}$ which represent the time necessary under the given conditions to bring about respectively 10% and 90% of the increase in torque ($\Delta$torque).

The determinations were carries out at 170° C., using a slit width of 0.2 mm, an oscillation angle of about 0.5° and an oscillation frequency of 0.83 Hz.

The results are given in Table 1. For comparison, the values are mentioned of analogous experiments carried out using 0.01 mole of dicumyl peroxide (Compound A) and 0.01 mole of 1-phenyl-3,3-di(tobutylperoxy)-1-propene (Compound B: an unsaturated peroxide according to U.S. Pat. No. 3,980,629).

From the $t_{10}$ and $t_{90}$ values found it appears that the processing range of the present peroxides is similar to that of dicumyl peroxide (A) and in several cases even exceeds it, whereas the processing range of the peroxide (B) disclosed in U.S. Pat. No. 3,980,629 is narrower.

TABLE

| Compound | Gottfert Elastograph Data | |
|---|---|---|
|  | $t_{10}$ (min) | $t_{90}$ (min) |
| 1 | 1.4 | 10 |
| 2 | 1.3 | 9 |
| 3 | 1.4 | 10 |
| 4 | 1.2 | 9 |
| 5 | 1.1 | 6 |
| 6 | 1.5 | 10 |
| 7 | 1.5 | 9 |
| A | 1.0 | 8 |
| B | 0.5 | 4 |

EXAMPLE 9

The peroxides described in Example 1 and 5 were tested as cross-linking agents for polyethylene. To that end, 0.01 equivalent of the peroxide (=0.01 mole of Compound 1, and 0.005 moles of Compound 5, respectively) was mixed on a roll mill for 3 minutes at 120°-130° C. with 100 g of polyethylene (Lupolen ® 1810 H, ex BASF). Subsequently, the cross-linking behaviour was determined with the aid of the Göttfert Elastograph described in Example 8.

The $t_{10}$, $t_{90}$ and $\Delta$torque values obtained are listed in Table 2. The Tables also gives the compression moulding temperatures and the compression moulding times applied in the cross-linking processes.

The cross-linked products obtained were tested for odour and blooming and the following properties were measured.

The tensile strength, the 100, 200 and 300% moduli and the elongation at break were determined in accordance with ISO-standard R37 type 1.

The hardness was determined in accordance with ASTM D2240.

The gel fraction was measured in conformity with the standards B5 5468-1977 and ANSI/ASTM D2765-68(1972). In this test the percentage polymer is determined which does not dissolve in boiling xylene under the test conditions. This parameter is a measure of the degree of cross-linking and hence of the efficiency of the peroxide.

The results are given in Table 2. Table 2 also contains the results of a comparative experiment carried out with 0.01 moles of dicumyl peroxide (Compound A).

The results obtained show that as cross-linking agents for polyethylene, the peroxides according to the invention are a good alternative to dicumyl peroxide.

TABLE 2

| Polyethylene Cross-linked with Compounds 1,5 and A | | | |
|---|---|---|---|
| Compound | 1 | 5 | A |
| $t_{10}$ (min) | 1.4 | 0.9 | 1.1 |
| $t_{90}$ (min) | 10.9 | 7.0 | 9.2 |
| $\Delta$torque (Nm) | 0.53 | 0.40 | 0.51 |
| Compression moulding temp. (°C.) | 170 | 170 | 170 |
| Compression moulding time (min) | 25 | 20 | 20 |
| Tensile strength (MPa) | 20.1 | 19.6 | 19.8 |
| Modulus 100% (MPa) | 8.0 | 7.9 | 7.9 |
| Modulus 200% (MPa) | 8.4 | 8.2 | 8.3 |
| Modulus 300% (MPa) | 10.6 | 9.8 | 10.6 |
| Elong. at break (%) | 400 | 460 | 410 |
| Hardness °Shore D | 48 | 49 | 49 |
| Gel fraction (%) | 92 | 87 | 89 |
| Odour | none | none | yes |
| Blooming after 1 week | none | none | yes |

We claim:

1. A peroxide of the formula

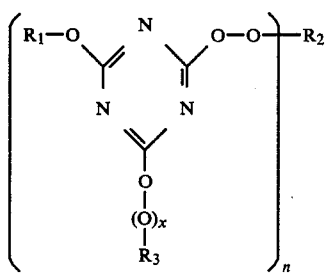

(I)

where
n is 1 or 2
when n = 1, $R_1$ is selected from the group consisting of an allyl group, a methallyl group and a crotyl group, $R_2$ is selected from the group consisting of an unsubstituted alkyl group, an alkyl group substituted with at least one hydroxyl group, an unsubstituted alkenyl group, an alkenyl group substituted with at least one hydroxyl group, an unsubstituted aralkyl group, and an aralkyl group substituted on the aromatic ring with at least one substituent selected from the group consisting of alkyl groups, alkenyl groups and mixtures thereof, $R_2$ having 4–20 carbon atoms when $R_2$ is nonaromatic and 7–20 carbon atoms when $R_2$ is aromatic, x is selected from the group consisting of 0 and 1, when x=0, $R_3=R_1$, when x=1, $R_3=R_2$; and when n=2, $R_1$ is selected from the group consisting of an allyl group, a methallyl group and a crotyl group, $R_2$ is selected from the group consisting of an unsubstituted alkylene; an unsubstituted alkynylene; and alkylene substituted with one or more substitutents selected from the group consisting of alkyl groups, alkenyl groups and mixtures thereof; and an alkynylene substituted with one or more substituents selected from the group consisting of alkyl groups, alkenyl groups and mixtures thereof, $R_2$ having 4–20 carbon atoms, x=0, and $R_3=R_1$.

2. The peroxide according to claim 1, characterized in that n=1, $R_1$ is an allyl group, and $R_2$ is selected from the group consisting of an unsubstituted alkyl group, an alkyl group substituted with a hydroxyl group, an unsubstituted alkenyl group, and alkenyl group substituted with a hydroxyl group, an unsubstituted aralkyl group and an aralkyl group substituted on the aromatic ring with a substituent selected from the group consisting of an alkyl group and an alkenyl group, $R_2$ having 4–8 carbon atoms when $R_2$ is non-aromatic and 9–12 carbon atoms when $R_2$ is aromatic.

3. A peroxide according to claim 1, characterized in that the peroxide is selected from the group consisting of 2-t-butylpeoxy-4,6-diallyloxy-1,3,5-trazine, 2-t-amylperoxy-4,6-diallyloxy-1,3,5-triazine, 2,4-di-t-butylperoxy-6-allyloxy-1,3-5-triazine, 2-(4-hydroxy-2methylpentyl-2 peroxy)-4,6-diallyloxy-1,3,5-triazine, 2-(2,4,4-trimethylpentyl-2-peroxy)-4,6-diallyloxy-1,3,5-traizine, 2,5-dimethyl-2,5-di(4,6-diallyloxytriazinyl-2-peroxy)-hexane, and 2,5-dimethyl-2,5-di(4,6-diallyloxytriazinyl-2-peroxy)-hexyne.

* * * * *

UNITED STATES PATENT AND TRADEMARK OFFICE
CERTIFICATE OF CORRECTION

PATENT NO. : 4,855,428

DATED : August 8, 1989

INVENTOR(S) : Johannes P.J. VERLAAN et al

It is certified that error appears in the above-identified patent and that said Letters Patent is hereby corrected as shown below:

Col. 1, line 9, change "ot" to --to--;

line 26, change "rick" to --risk--;

line 59, after "34" insert --,--.

Col. 2, line 26, change "aleknyl" to --alkenyl--;

line 61, change "meansing" to --meaning--.

Col. 3, line 3, change "hydroperoixdes" to --hydroperoxides--;

line 36, delete "to" (first occurrence only);

line 37, after "2-t-butylperoxy-4,6-diallyloxy-1,3,5-triazine" insert --,--;

line 52, change "phas" to --phase--.

Col. 4, line 4, change "acrylonitrile-butadien-styrene" to --acrylonitrile-butadiene-styrene--;

line 13, change "presen" to --present--;

line 50, change "wree" to --were--;

line 62, change "repated" to --repeated--.

UNITED STATES PATENT AND TRADEMARK OFFICE
CERTIFICATE OF CORRECTION

PATENT NO. : 4,855,428

DATED : August 8, 1989

INVENTOR(S) : Johannes P.J. VERLAAN et al

It is certified that error appears in the above-identified patent and that said Letters Patent is hereby corrected as shown below:

Col. 5, line 4, change "2-(2-4,4-trimethylpenytyl-2-peroxy)4,6-diallyloxy-1,3,5-" to --2-(2,4,4-trimethylpenytyl-2-peroxy)-4,6-diallyloxy-1,3,5- --.

line 17, change "2-(40-hydroxy-2mtheylpentyl-2-peroxy)-4,6-diallyloxy-" to --2-(4-hydroxy-2-methylpentyl-2-peroxy)-4,6-diallyloxy---;

line 22, change "4-hydroxy-2methylpentyl-2-hydroperoxide" to --4-hydroxy-2-methylpentyl-2-hydroperoxide--;

line 37, change "2,4-dicholor-6-allylox-" to --2,4-dichloro-6-allylox---;

line 47, change "benxane" to --hexane--.

Col. 6, line 7, change "(-0.01" to --(=0.01--;

lines 13-14, change "Katushcuk and Cummi" to --Kautshcuk und Gummi--.

UNITED STATES PATENT AND TRADEMARK OFFICE
CERTIFICATE OF CORRECTION

PATENT NO. : 4,855,428

DATED : August 8, 1989

INVENTOR(S) : Johannes P.J. VERLAAN et al

It is certified that error appears in the above-identified patent and that said Letters Patent is hereby corrected as shown below:

Claim 1, col. 7, line 56, change "where" to --wherein--;
       col. 8, line 21, change "and" to --an--;
               line 37, change "and" to --an--.

Signed and Sealed this

Third Day of November, 1992

Attest:

DOUGLAS B. COMER

Attesting Officer     Acting Commissioner of Patents and Trademarks